United States Patent
Stufano et al.

(10) Patent No.: US 10,961,387 B2
(45) Date of Patent: Mar. 30, 2021

(54) METHODS FOR PRODUCING BIOPOLYMER MATRIX COMPOSITES

(71) Applicant: EGGPLANT S.R.L., Polignano A Mare (IT)

(72) Inventors: Paolo Stufano, Polignano A Mare (IT); Emanuele Vito Carofiglio, Polignano A Mare (IT); Antonio Goffredo, Monopoli (IT); Maurizio Servili, Montefalco (IT); Domenico Centrone, Polignano A Mare (IT)

(73) Assignee: EGGPLANT S.R.L., Polignano A Mare (IT)

( * ) Notice: Subject to any disclaimer, the term of this patent is extended or adjusted under 35 U.S.C. 154(b) by 399 days.

(21) Appl. No.: 15/472,751

(22) Filed: Mar. 29, 2017

(65) Prior Publication Data

US 2017/0260390 A1    Sep. 14, 2017

Related U.S. Application Data

(63) Continuation of application No. PCT/EP2015/071793, filed on Sep. 22, 2015.

(30) Foreign Application Priority Data

Oct. 1, 2014  (IT) .......................... TO2014A000786

(51) Int. Cl.
| | | |
|---|---|---|
| C08L 67/04 | (2006.01) | |
| C12P 7/62 | (2006.01) | |
| C02F 9/00 | (2006.01) | |
| C08L 101/16 | (2006.01) | |
| C08L 97/02 | (2006.01) | |
| C08L 99/00 | (2006.01) | |
| C02F 1/44 | (2006.01) | |
| C02F 3/34 | (2006.01) | |
| C02F 101/30 | (2006.01) | |
| C02F 103/32 | (2006.01) | |

(52) U.S. Cl.
CPC .............. *C08L 67/04* (2013.01); *C02F 9/00* (2013.01); *C08L 97/02* (2013.01); *C08L 99/00* (2013.01); *C08L 101/16* (2013.01); *C12P 7/625* (2013.01); *C02F 1/441* (2013.01); *C02F 1/442* (2013.01); *C02F 1/444* (2013.01); *C02F 3/341* (2013.01); *C02F 2101/30* (2013.01); *C02F 2103/322* (2013.01); *Y02E 50/30* (2013.01); *Y02W 10/37* (2015.05); *Y02W 10/40* (2015.05)

(58) Field of Classification Search
CPC .......... C12P 7/625; C08L 97/02; C08L 99/00; C08L 101/16; C08L 67/04; C02F 9/00; C02F 3/341; C02F 1/441; C02F 1/442; C02F 1/444; C02F 2101/30; C02F 2103/322; Y02W 10/37; Y02W 10/45; Y02W 10/40; Y02E 50/343; Y02E 50/30

USPC ........................................................... 524/35
See application file for complete search history.

(56) References Cited

U.S. PATENT DOCUMENTS

| | | |
|---|---|---|
| 7,141,400 B2 | 11/2006 | Yu |
| 7,887,893 B2 | 2/2011 | Billington et al. |
| 8,187,462 B2 | 5/2012 | Bengtsson et al. |
| 8,263,373 B2 | 9/2012 | Herrema et al. |
| 2002/0061944 A1* | 5/2002 | Asrar ...................... C08L 67/04 524/130 |
| 2006/0088921 A1 | 4/2006 | Yu |
| 2012/0085701 A1 | 4/2012 | Evans et al. |
| 2013/0040351 A1 | 2/2013 | Liu et al. |
| 2013/0199997 A1 | 8/2013 | Werker et al. |
| 2014/0377819 A1 | 12/2014 | Yu |

FOREIGN PATENT DOCUMENTS

| | | |
|---|---|---|
| WO | 9635641 | 11/1996 |
| WO | 9928490 A1 | 6/1999 |
| WO | 2005123603 A1 | 12/2005 |
| WO | 2009093367 A1 | 7/2009 |
| WO | 2012166822 A2 | 12/2012 |
| WO | 2013058761 A1 | 4/2013 |

OTHER PUBLICATIONS

Olipha News Issue 02 (Year: 2014).*
Coats, et al., "Synthesis of Polyhydroxyalkanoates in Municipal Wastewater Treatment" Water Environment Research, 79(12):2396-2403, 2007.
Cerrone, et al., "Biological Treatment of Two-Phase Olive Mill Wastewater (TPOMW, alpeorujo): Polyhydroxyalkanoates (PHAs) Production by Azotobacter Strains", Journal of Microbiology and Biotechnology, 20(3):594-601, 2010.
Mato, et al., "Valuable product production from wood mill effluents", Water Science & Technology—WST, 62, No. (10):2294-2300, 2010.
Elodie Bugnicourt: Olipha Functional Sustainable Packaging, "The Oli-Pha Solution" (Project description) www.olipha.eu, Sep. 1, 2013, pp. 1-6.

(Continued)

Primary Examiner — Angela C Scott
(74) Attorney, Agent, or Firm — Edgar W. Harlan; Carolyn S. Elmore; Elmore Patent Law Group, P.C.

(57) ABSTRACT

A bio-derived polymer matrix composite originating from a single wastewater stream and a method for the production of such bio-derived polymer matrix composites from a single wastewater stream are herein disclosed. The process disclosed allows production of both the bio-derived polymer matrix and the additive, the main constituents of the composite, at the same time from a unique wastewater stream source. In a preferred embodiment, this invention is applied but not limited to the production of a polyhydroxyalkanoate (PHA) composite from a single olive mill wastewater (OMW) stream. An application of such composites is represented by but not limited to the use as materials to make agricultural items.

20 Claims, 1 Drawing Sheet

(56) References Cited

OTHER PUBLICATIONS

Olipha Functional Sustainable Packaging (Project description), www.olipha.eu, Jun. 24, 2013.
Olipha Functional Sustainable Packaging: "The Oli-PHA Solution", www.olipha.eu, Jun. 24, 2013.
Bhardwaj, U. et al., "Polyhydroxyalkanoates (PHA)-cellulose based nanobiocomposites for food packaging applications", ACS Symposium Series, vol. 1162, Jul. 22, 2014, 275-314.
Russo, C., "A new membrane process for the selective fractionation and total recovery of polyphenols, water and organic substances from vegetation waters (VW)", vol. 288, Issues 1-2, Feb. 1 2007, 239-246.

* cited by examiner

METHODS FOR PRODUCING BIOPOLYMER MATRIX COMPOSITES

RELATED APPLICATION(S)

This application is a continuation of International Application No. PCT/EP2015/071793, which designated the United States and was filed on Sep. 22, 2015, published in English.

This application claims priority under 35 U.S.C. § 119 or 365 to Italy, Applications No. TO2014A000786, filed Oct. 1, 2014. The entire teachings of the above applications are incorporated herein by reference.

TECHNICAL FIELD OF THE INVENTION

This invention relates to bio-derived polymer matrix composites which are produced from waste. More particularly, the invention relates to aforementioned bio-composites obtained from a single wastewater stream and a method for producing the same by an integrated closed process while purifying the wastewater at once.

BACKGROUND OF THE INVENTION

Conventional fossil carbon derived plastics represent an important concern for the environment, being at once a problem for the limited fossil resources and one of the first source of pollution, increasing interest in using bio-derived and bio-degradable polymers to produce sustainable eco-friendly materials as an alternative to conventional plastics. Examples of bio-derived and bio-degradable polymers are, among others, poly-lactic acid (PLA), starch and polyhydroxyalkanoates (PHAs).

Although the production of biopolymers from natural sources is currently on stream, research is still ongoing to find effective methods of sustainable biopolymer production from sources different from those destined for the human food supply. The industrial production of biopolymers from waste is highly desirable and the object of many research efforts.

Beside ethical concerns, producing biopolymers from waste is intended to reduce their cost since the high price of biopolymers represents the primary barrier for their market penetration. Suitable waste streams for biopolymer production include industrial and urban wastewater.

An important concern about polymers, in general, and more specifically about biopolymers, is related to their physical and mechanical properties. In order to obtain the desired properties, biopolymers are usually loaded with different fillers. Since fillers are often expensive and used in high mass percentage (1-40%) in the final composite, natural fillers, such as natural fibers, have been proposed to decrease the cost of the final polymer matrix composite. When a bio-derived polymer matrix and natural fillers are used, the resulting composite is absolutely a green plastic. As for biopolymer matrix materials, waste-derived natural fillers as additives are highly desirable and object of many research efforts.

Several industrial processes produce a wastewater stream. Such waste is often rich in organic carbon content, especially in the case of agro-industrial processes, as for instance, the production of milk, cheese, fruit juice, sugar and olive oil. Other examples of common wastewater streams which are rich in organic carbon are pulp and paper-mill wastewater, municipal wastewater and farm wastewater. These aqueous liquid streams have a high environmental impact due to their high Chemical Oxygen Demand (COD). At the same time, however, a high COD value represents a hidden source of value, as the added-value molecules can be separated from the wastewater and the remaining organic content may be used as raw material for biopolymer production. Researchers have been working for a long time on size-exclusion membrane filtration techniques that are ideal candidates for separating valuable chemicals from waste streams.

Several patents and patent applications describe methods for treating and purifying high COD wastewater streams. These methods are usually based on membrane filtration techniques with a final reverse osmosis (RO) step to generate ultra-pure water, which can be re-used in the process or collected for other applications. The extracted organic matter may be used to make compostable materials or for bio-gas production by microbial digestion, which allows the abatement of COD in the liquid stream. The order of the filtration process and the microbial digestion can be inverted depending on the specific process considered.

Examples of wastewater purifying treatment by membrane filtration, microbial digestion and combined methods are disclosed in the following documents and in the references of the patent and non-patent literature cited therein.

WO 2013/058761 describes a system for wastewater treatment, to be applied to distillery waste streams, reducing the organic content by means of interconnected components of a coarse suspended solids removal unit, a coarse filtration unit, an ultrafiltration unit (UF), a nanofiltration unit (NF) and a reverse osmosis network. The output from such a system may meet drinking water standards.

US 2012/0085701 also describes a process for treating a water stream containing dissolved organic carbon, such as pulp or paper mill wastewater, to reduce the organic content by means of a bioreactor for biogas production, possibly a membrane bioreactor, and membrane filtration modules, i.e. nanofiltration and reverse osmosis, applicable to domestic and industrial effluents. The purpose of the process is the purification of organic carbon containing water stream for water disposal or recycling.

EP 0824503 describes a multi-stage system for producing high yields of drinking water from organically contaminated wastewater. The system comprises, beside other treatments such as ultrafiltration and oxidation processes, a double (anaerobic and aerobic) microbial digestion to reduce the organic carbon load and multiple reverse osmosis steps to produce ultra-pure water to be used in beverages.

An interesting industrial wastewater stream is olive mill wastewater (OMW). OMW is a difficult waste to treat for water purification, as it features a very high organic carbon content, and/or for bio-gas production, due to the high content of polyphenols. It can be treated by membrane filtration techniques to separate polyphenols as high commercial valuable molecules. EP 1773721 describes a process for recovering the components of olive mill wastewater with membrane technologies. A multi-step filtration process (microfiltration (MF), ultrafiltration (UF), nanofiltration (NF), reverse osmosis (R0)) is used to recover polyphenol solutions and purified water from OMW. The residual organic matter, beside polyphenols, resulting from the different filtration steps has been proposed for use as a fertilizer or for biogas production.

In addition to natural polymers directly extracted from natural feedstock, different natural chemical substances can be used as raw materials for biopolymer production (see, e.g., *Handbook of Biopolymers and Biodegradable Plastics*, S. Ebnesajj ad, Ed., 2012). For instance, unsaturated fatty acids deriving from vegetable oils are useful monomers for polyamide (PA) synthesis, through subsequent dimerization and poly-condensation processes, or for microbial polyhydroxyalkanoate (PHA) production. Among others classes of natural chemicals, sugars represent a great platform for biopolymer synthesis. The use of sugars for this purpose includes (i) lactide production through sugar hydrolysis, fermentation to produce lactic acid and its condensation; lactide is the monomer used to produce poly(lactic acid) (PLA) through ring opening and polymerization; (ii) production of chemicals such as bioethanol, ethylene, acrylic acid and its derivatives, acrolein, glycerol, 1,3-propanediol and other polyols, hydroxymethylfurfural and its derivatives; all these bio-derived chemicals are useful monomers for the production of a variety of polymers; (iii) direct production of polymeric bio-materials, such as PHAs, by living microorganisms through microbial digestion of naturally occurring nutrients, such as sugars or volatile fatty acids (VFAs).

Currently, different processes are on stream, based on the use of sugars from renewable resources for the production of biopolymers. Nevertheless, the majority of these processes employ edible biomasses like sugar cane, maize, starch crops, etc. Municipal and industrial wastewater streams, especially those coming from the agro-food chain, are usually characterized by a high organic carbon load and, in particular, by a considerable concentration of sugars. A cost-efficient recovery and/or utilization of the sugar content in this waste can enable the production of all the bio-based monomers and polymers described in the previous paragraph.

The production of polyhydroxyalkanoates from high sugar content waste has been disclosed. U.S. Pat. No. 7,141,400, US 2006/0088921 (Yu) and WO 2013/072723 describe the microbial production of PHAs from high sucrose content waste such as molasses, byproduct of sugar production. Nevertheless, microbial digestion for production of PHAs often exploits other classes of natural substances (such as protein or fatty acids) contained in the waste in addition to sugars (see, e.g., M. Koller et al. *Food Technol. Biotechnol.* 2010 48:255-269; C. Du et al. *Curr. Chem. Biol.* 2012; J. G. C. Gomez et al. in Advances in Applied Biotechnology, 2012, 6:14-25; J.-Y. Chee et al. in *Current Research, Technology and Education Topics in Applied Microbiology and Microbial Biotechnology,* 2010), so that different classes of wastewater streams have been considered for PHA production, as reported in US 2013/0040351, US 2013/0199997 and WO 2012/166822, U.S. Pat. Nos. 8,187,462 and 8,263,373.

Research efforts have been spent to produce polyhydroxyalkanoates (PHAs), a class of bio-derived and biodegradable thermoplastic polymers, from OMW, but an effective industrial process has yet to be disclosed. Examples of this technology have been reported at the lab scale by bacterial fermentation of untreated diluted OMW. (G. A. Martinez et al. *Env. Eng. Manag. J.* 2013, 12:97-100; F. Cerrone at al. *J. Microbiol. Biotechnol.* 2010; M. Beccari et al. *J. Chem. Technol. Biotechnol.* 2009, 84:901-908).

Among plastic composites, biopolymer-matrix composites obtained by combining natural reinforcing agents such as natural fibers with biodegradable and bio-derived resins are attractive because they are ecofriendly, sustainable and degradable by composting (see, e.g., *Polymer Composites: Volume* 1, S. Thomas et al., Eds, Wiley-VCH 2012). A number of natural fibers and bio-derived reinforcing agents such as jute, flax, sisal, coir etc. have been mixed with biopolymers such as PLA, starch and PHAs among the others (see, e.g., J. Sahari et al. *Rev. Adv. Mater. Sci.* 2011, 30:166-174; P. Asokan et al. *Rev. Adv. Mater. Sci.* 2012, 30:254-261). Agricultural residues are a huge industrial byproduct (billions of tons per year worldwide) and their use as reinforcement for polymer composites is a realistic alternative to their disposal or burning. The use of natural fibers provides many advantages, including low cost, abundance, low density, high specific properties and, clearly, biodegradability. These bio-based composites may be used effectively in many applications such as mass-produced consumer products. As for conventional plastics, the addition of natural additives may improve the physical and mechanical properties of the polymeric resin.

For the natural fiber biopolymer-matrix composites not only an improvement of physical and mechanical properties has been reported but also an improved biodegradability (see, e.g., O. Faruk et al. *Macromol. Mater. Eng.* 2014, 299:9-26; H. Ku et al. *Composites Part B Eng.* 2011, 42:856-873; P. M. Visakh et al. *Advances in Natural Polymers,* S. Thomas et al., Eds., Springer 2013; M. Avella et al. *Materials,* 2009, 2:911-925; C.-S. Wu, *Carbohydrate Polym.* 2012, C.-S. Wu, *Polym. Degrad. Stabil.* 2012, 97:64-71).

PHAs are representative of the utility of biopolymer-matrix composites with natural reinforcing agents. Many research efforts have been spent to improve the biodegradability and physical properties of PHAs by addition of natural reinforcing agents (see, e.g., C.-S. Wu et al. *Polym. Degrad. Stabil.* 2014, 99:274-282; C.-S. Wu, *Polym. Degrad. Stabil.* 2013, 98:1473-1480; V. Nagarajan et al. *Ind. Crops Prod.* 2013, 42:461-468; Y. S. Salim et al. *Appl. Biochem. Biotechnol.* 2012, 167:314-326; P. Mousavioun et al. *Polym. Degrad. Stabil.* 2012, 97:1114-1122). U.S. Pat. No. 7,887,893 describes a bacterial polyhydroxyalkanoate polymer/natural fibers composite that aims to be a biomaterial with improved properties compared to PHA alone while retaining its biodegradability properties. U.S. Pat. No. 6,903,053 describes the use of PHA copolymers for agricultural items that come in contact with plants and methods for the controlled release of chemicals from such materials.

There is a need for methods of producing a low cost natural biopolymer-matrix composite which is useful in applications, for example, in agriculture and packaging.

It is to be understood that the foregoing is not an admission that anything discussed above is citable as prior art or within the common general knowledge.

SUMMARY OF THE INVENTION

The present invention is aimed at solving various problems in the state of the art by providing: (i) a natural biopolymer-matrix composite obtained from a single wastewater stream; (ii) simultaneous water purification and natural additive recovery from a single wastewater stream; and (iii) a concentrated solution with high organic carbon load to be used as substrate for biopolymer production, thus reducing the volume of solution to be treated with consequent advantages in terms of cost and ease of the biopolymer production process.

Thus, it is an object of the present invention to provide a bio-derived polymer and polymer-matrix composite originated from a single wastewater stream and to provide a method for the production of such bio-derived polymer-matrix composites from a single wastewater stream.

It is another object of the invention to treat the organic carbon rich wastewater stream, after a pretreatment, by means of membrane filtration techniques to concentrate the organic load.

It is also another object of the invention to provide in the filtration steps at least a microfiltration (MF) step which produces a concentrate rich in micro-sized materials that, when dried and possibly subjected to further treatments, are used as natural additives, serving for example, as reinforcing agents for the composite.

Additionally, it is an object of certain embodiments of this invention to provide a further treatment of the MF permeate in successive steps comprising at least one reverse osmosis (RO) step which affords ultrapure water and a high organic loaded concentrate.

It is another object of the present invention to provide a method for using the RO concentrate, optionally combined with concentrates resulting from previous filtration steps, as the substrate for the production of biopolymers, which are used as a polymer matrix of the composite.

A composite obtained from a unique wastewater stream represents an improved product compared to the standard biopolymer obtainable by conventional biological/chemical treatments of waste. Membrane filtration has been used in the purification of water or the recovery of added value molecules from waste. However, known processes for wastewater treatment do not use the waste liquid stream as a source of natural micro-sized natural additives for polymer-matrix composites or increase the concentration of organic load in the filtration concentrate for use as a suitable high COD substrate for biopolymer production.

In a preferred embodiment, the present invention provides a method of producing a polyhydroxyalkanoate (PHA) composite from a single wastewater stream, such as an olive mill wastewater (OMW) stream.

In one embodiment, the invention provides a method of producing a biopolymer, comprising the steps of: (a) subjecting wastewater, wherein said wastewater comprises organic carbon and organic solids, to (i) microfiltration, thereby producing a permeate and a concentrate; and optionally further subjecting the first permeate to at least one process selected from (ii) ultrafiltration; and (iii) nanofiltration; wherein each of steps (ii) and (iii) produces a further permeate comprising organic carbon and a concentrate, wherein the permeate of the final of steps (i), (ii) and (iii) is the final permeate; and the input for each of steps (ii) and (iii) is the permeate of the immediately preceding step; (b) subjecting the final permeate to reverse osmosis, thereby producing a final concentrate, wherein said final concentrate comprises organic carbon; (c) subjecting the final concentrate to a chemical or biological process that produces a biopolymer, thereby producing a biomass comprising the biopolymer; and (d) isolating the biopolymer from the biomass.

In one embodiment, the invention provides a method of producing a biopolymer matrix composite, comprising the steps of: (a) subjecting wastewater, wherein said wastewater comprises organic carbon and organic solids, to (i) microfiltration, thereby producing a permeate and a concentrate; and optionally further subjecting the first permeate to at least one process selected from (ii) ultrafiltration; and (iii) nanofiltration; wherein each of steps (ii) and (iii) produces a further permeate comprising organic carbon and a concentrate, wherein the permeate of the final of steps (i), (ii) and (iii) is the final permeate; and the input for each of steps (ii) and (iii) is the permeate of the immediately preceding step; (b) subjecting the final permeate to reverse osmosis, thereby producing a final concentrate, wherein said final concentrate comprises organic carbon; (c) isolating microparticles from the concentrate of step a(i); (d) subjecting the final concentrate to a chemical or biological process that produces a biopolymer, thereby producing a biomass comprising the biopolymer; (e) isolating the biopolymer from the biomass; and (f) combining the biopolymer and the microparticles of step (c), thereby producing the biopolymer matrix composite. In preferred embodiments, the wastewater is pretreated to remove coarse solids and emulsions prior to step (a).

DETAILED DESCRIPTION OF THE INVENTION

The present invention relates to the finding that a wastewater stream comprising organic solids can be used as the starting material for production of a biopolymer matrix composite which is a suitable biodegradable and low-cost material useful, for example, in agricultural and packaging applications.

Figure 1:
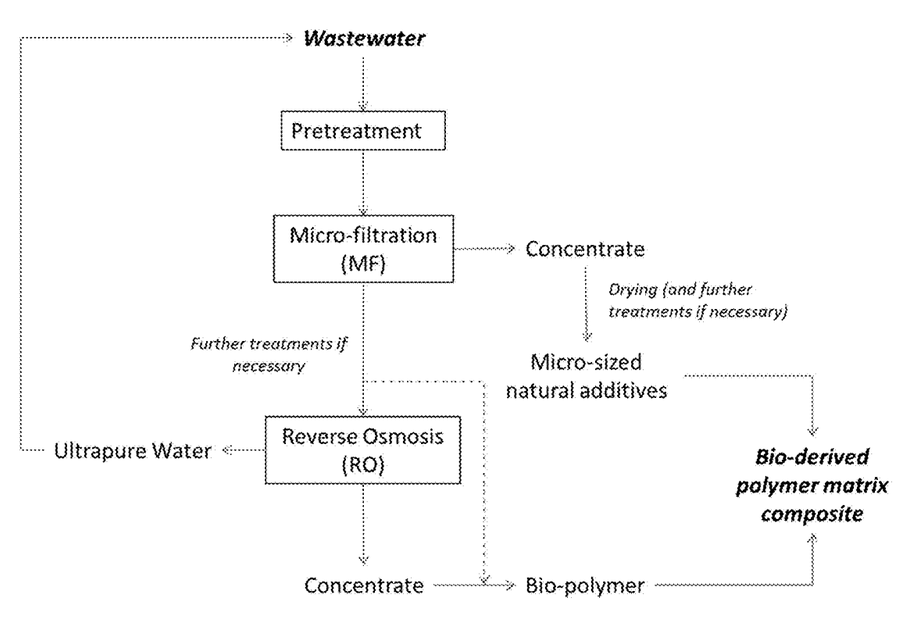
The FIGURE is a schematic representation of an integrated closed process for producing a composite material comprising a biopolymer produced using a part of the waste stream as a carbon source and natural additives produced from another part as natural additives to be used as filler of the composite with the former biopolymer as matrix.

An embodiment of the process of the invention is illustrated schematically in The FIGURE. Wastewater from a wastewater stream is optionally pretreated to remove coarse solids and/or emulsions. The pretreated wastewater is subjected to microfiltration and the resulting concentrate is diverted and dried to obtain microparticles. The microfiltration permeate is optionally further treated, for example with ultrafiltration and/or nanofiltration, and the final permeate, i.e., the permeate from the last of the microfiltration, ultrafiltration or nanofiltration step, is subjected to reverse osmosis. To the concentrate resulting from reverse osmosis is optionally added the concentrate(s) from the ultrafiltration and/or nanofiltration steps to produce a combined concentrate. The reverse osmosis concentrate or the combined concentrate is subjected to a chemical or biological process which produces a biopolymer.

The biopolymer is then combined with the microparticles from the microfiltration concentrate to produce a polymer matrix composite.

In one embodiment, the biopolymer is produced by a biological process, for example, a process comprising aerobic digestion, such as microbial, preferably bacterial aerobic digestion, and, optionally, further comprising anaerobic digestion. In one embodiment, the biological process comprises anaerobic digestion followed by aerobic digestion.

In a preferred embodiment, the method of producing a biopolymer matrix composite comprises the steps of: (a) subjecting wastewater, wherein said wastewater comprises organic carbon and organic solids, to (i) microfiltration, thereby producing a permeate and a concentrate; and optionally further subjecting the permeate to at least one process selected from (ii) ultrafiltration; and (iii) nanofiltration; wherein each of steps (ii) and (iii) produces a permeate comprising organic carbon and a concentrate, wherein the permeate of the final of steps (i), (ii) and (iii) is the final permeate; and the input for each of steps (ii) and (iii) is the permeate of the immediately preceding step; (b) subjecting the final permeate to reverse osmosis, thereby producing a final concentrate, wherein said final concentrate comprises organic carbon; (c) isolating microparticles from the concentrate of step a(i); (d) subjecting the final concentrate to anaerobic digestion; (e) subjecting the product of step (d) to microbial aerobic digestion to produce a biomass comprising a biopolymer; (f) isolating the biopolymer from the biomass; and (g) combining the biopolymer and the microparticles of step (c), thereby producing the biopolymer matrix composite.

A "biopolymer" as this term is used herein, is a biodegradable carbon-based polymeric material which can be extracted or produced by synthetic, i.e. not involving living microorganisms, such as polymerization of bio-derived monomers, and natural, i.e., involving microorganisms, such as bacterial digestion, processes from natural sources. Examples of biopolymers include those which are produced using wastewater, and chemicals or monomers extracted therefrom, as a natural carbon source.

The term "wastewater", as used herein, refers to any liquid aqueous stream produced by human processes, such as industrial, farm or agricultural processes, or urban wastewaters, that contains a high level of organic carbon. The amount of organic carbon in the wastewater can be measured by the Chemical Oxygen Demand (COD), a measure of the oxygen required to fully oxidize the organic material in a water sample. Such wastewaters are typically destined for disposal at dedicated sites or further treatment prior to disposal to reduce their environmental impact.

The term "composite" refers to a complex material formed by at least two components, one of which is a matrix in an amount typically in the range of about 50% to about 99.9% of the total weight of the composite. A composite is formed by combining the matrix with an additive or filler which is typically used in an amount ranging from about 0.1% to about 50% by weight relative to the weight of the composite. The presence of the additive improves the biodegradability of the matrix compared to the matrix alone, modulates the mechanical characteristics of the matrix alone according to the desired application and reduces the cost of the composite when the additive is less expensive than the matrix.

The wastewater can be obtained from any wastewater stream, but preferably is wastewater having a high Chemical Oxygen Demand, for example a COD greater than about 50 mg/L, 200 mg/L, 500 mg/L or 1000 mg/L. The wastewater preferably further comprises organic solids, such as solid particulates.

In one embodiment, the wastewater is treated prior to step (a) of the method to remove coarse suspended solids and/or emulsions. This treatment can comprise filtering with a large pore filter, for example, with pore sizes in the range of 0.1 to 2 mm, centrifugation at low rotational speeds and/or flocculation. In this embodiment, the resulting filtrate or supernatant is pretreated wastewater and is the feedstock for step (a) in the methods of the invention.

In one embodiment the wastewater in step (a) contains micrometer-sized suspended solids and is subjected to a filtration process. In one embodiment, the wastewater is sent to a membrane microfiltration module. Suitable filtration modules include, for example, those with tubular ceramic and/or polymeric membranes with controlled pore size. The direction of the wastewater flow, which is moved by mechanical pumps, is tangential to the membrane, producing a permeate and a concentrate. The permeate is the solution that passes through the membrane and contains the components which have a size smaller than the cut-off size of the membrane. The concentrate is a solution rich in components which have a size greater than the cut-off size of the membrane and thus cannot pass through the membrane.

In a preferred embodiment, the wastewater is subjected to microfiltration with a ceramic or a polymeric membrane. Ceramic membranes have a superior resistance despite their higher cost than the polymeric ones. Diafiltration, a process of diluting and recirculating the concentrate again through the same membrane from which it has been isolated, is optionally used in order to maximize the recovery of chemical components in the permeate which is then sent to the next filtration step or reverse osmosis. The use of a microfiltration membrane with pore dimensions from 100 µm down to 0.1 µm, preferably in the range of 0.2-2 µm, allows isolation of solid particles in the concentrate having dimensions from about 100 µm down to about 0.1 µm. Such particles are used, preferably after appropriate treatment, as fillers in the final biopolymer matrix composite. For example, the microparticles from the MF concentrate can be dried and used directly as fillers in the biopolymer matrix composites of the invention. Preferably, these microparticles are homogenized, for example, by milling. In a preferred embodiment, the microparticles are milled using a high energy beads mill. In one embodiment the microparticles have dimensions in the range of about 0.1 to 100 µm.

The permeate from the microfiltration step is optionally further filtered to separate different components from the liquid waste stream. For example, this permeate can be subjected to ultrafiltration (UF) and/or nanofiltration (NF). In a preferred embodiment of the invention, the permeate from a filtration step is used as the input flow for the subsequent filtration step. The concentrate from the UF and/or NF steps can be recovered, sent again through the filtration system or combined with other concentrates depending on the desired application. According to the present invention, the microfiltration concentrate is recovered to obtain natural micro-sized particles which are used as fillers in the final biopolymer-matrix composite.

In one embodiment, the microfiltration permeate is subjected to ultrafiltration. In a preferred embodiment, the cut-off size of the UF polymeric membrane used in the UF module is in the range of 1-50 kDa. This membrane allows the separation of a concentrate that is rich in macromolecules in the class of proteins and long chain fatty acids and/or supramolecular aggregates possibly present in the MF permeate. The UF concentrate is optionally subjected to diafiltration and then eventually added to the RO concentrate to increase the organic matter to be used in the biopolymer production.

The UF permeate is optionally subjected to nanofiltration (NF). The NF concentrate is optionally subjected to diafiltration and then eventually added to the RO concentrate to increase the organic matter to be used in the biopolymer production. UF and/or NF of the permeate helps prevent RO membrane fouling and increases the lifetime of RO membrane. The final permeate, for example, the MF permeate, the UF permeate, or the NF permeate, depending on the filtration steps employed, is subjected to RO treatment. In a preferred embodiment the cut-off size of the RO polymeric membrane used in the RO module is in the range of 10-150 Da, for example about 150 Da, allowing the almost complete recovery of sugars, volatile fatty acids (VFAs), amino-acids and inorganic salts in the RO concentrate. A useful method for sugar recovery as simple carbohydrates from a wastewater stream is membrane filtration with membranes with a molecular cut-off smaller than about 150 Da. Since sugar units are usually greater than 150 Da in weight they are concentrated along with dissolved salts. The RO permeate is ultra-pure water that is useful for the dilution steps in the process, as in diafiltration and bacterial production of biopolymer.

The membrane life and efficiency in all the filtration steps described above is prolonged by periodic back washing of the membrane, i.e. flowing deionized water in the direction opposite to that of waste stream filtration through each filtering module.

In a preferred embodiment, the wastewater stream is Olive Mill Wastewater (OMW), a byproduct of olive oil production. OMW is a brown-greenish sludge produced in high quantity (40-120 L per 100 kg of olives) characterized by high COD values (up to 170 g/L) and slightly acidic pH (4-5). Among the variety of chemical components contained in OMW, polyphenols and carbohydrates are worthy of note. Polyphenols, which are valuable as antioxidizing agents, are present in OMW at up to 10% by weight, with the most abundant being oleuropein and hydroxytyrosol. Reducing sugars are present in OMW in total concentrations ranging from about 2 to 20% by weight and are suitable raw materials for biopolymer production. OMW represents a difficult waste stream to be treated for water purification and biopolymer-matrix composite production. The process of the invention efficiently produces a biopolymer composite from an aqueous waste stream such as OMW.

When the wastewater is OMW, the MF concentrate is a highly dense brown-greenish sludge. In a preferred embodiment, this sludge is dried, preferably air dried, and then finely homogenized by milling, for example with a high energy beads mill. Solid state FT-IR and thermogravimetric analyses on the isolated solid show the presence of cellulose, hemicellulose and lignin, as has been shown previously (Droussi et al. *J. Hazard. Mater.* 2009, 164:1281-1285; Garcia-Ibanez et al. *Fuel Process. Technol.* 2006, 87:103-107). These materials likely come from pressed olive residue from the olive-oil production process.

Cellulose and lignin are suitable substances for use as reinforcing natural agents in polymer matrix composites.

In a preferred embodiment, the MF permeate is subjected to UF. In a preferred embodiment, the cut-off size of the polymeric membrane used in the UF module is in the range of 1-50 kDa. This membrane allows the separation of a concentrate that is rich in macromolecules in the class of proteins and long chain fatty acids and/or supramolecular aggregates possibly present in the MF permeate. The UF concentrate is optionally subjected to diafiltration and then optionally added to the RO concentrate to increase the organic matter to be bacterially digested for the biopolymer production. The UF permeate of OMW is rich in polyphenols, sugars and salts and is optionally treated by means of NF to partially remove phenolic compounds, especially the high molecular weight ones, such as oleuropein, along with tannins and anthocyanins. In this embodiment, low molecular weight polyphenols, such as hydroxytyrosol, tyrosol, caffeic acid, p-coumaric acid, ferulic acid, etc. are distributed between the NF permeate and concentrate. UF and NF help to prevent RO membrane fouling and increase the lifetime of RO membrane. The complete removal of polyphenols from the solution treated by filtration is achieved by proper selection of NF membrane or by affinity chromatography as is known in the art. Polyphenols are preferably substantially removed prior to the bacterial biopolymer production step due to their anti-microbial activity, which can inhibit the bacterial growth.

Following removal of phenols, the RO concentrate is suitable for use as a medium for bacterial biopolymer production since the RO concentrate contains a high concentration of total reducing carbohydrates, up to 10% w/w. In a preferred embodiment, the RO concentrate is used as the medium containing the appropriate carbon sources, such as sugars and VFA, for bacterial production of polyhydroxyalkanoates (PHAs). The process can be performed on an industrial scale or at a small laboratory scale.

In certain embodiments, the biopolymer, such as PHA, is produced under fed-batch feeding conditions or in continuous flow mode. The fed batch process is coupled to the continuous flow filtration process by accumulating the waste stream concentrate and periodically subjecting it to bacterial digestion. The continuous production process comprises directly supplying the waste stream concentrate exiting from the filtration system into the bio-reactor line and automatically controlling the flow.

The fed-batch process PHA production example described herein is exemplary. The application of the present invention is not limited to the use of a batch process but also includes continuous operation mode and others as are known in the art.

Different approaches are possible for the production of PHAs from the wastewater concentrate. They include a digestion of the concentrate by mixed cultures of bacteria where a limitation of certain nutrients (e.g. phosphorus and/or nitrogen) promotes the growth of adaptive species which are able to accumulate PHAs. In a preferred embodiment, a single bacterial culture is used because of the higher percentage of PHA accumulated per unit of dry cellular biomass. A number of microbial genera, including both bacteria and archaea, can be used to produce and accumulate PHAs, (see, e.g., Koller, *Food Technol. Biotechnol.* 2010, 48, 255-269) including *Acidovorax, Acinetobacter, Actinobacillus, Actinomycetes, Aeromonas, Alcaligenes, Allochromatium, Anabaena, Aphanothece, Aquaspirillum, Asticcaulus, Axobacter, Azomonas, Aureobasidium, Azohydromonas, Azospirillum, Azotobacter, Bacillus, Beggiatoa, Beijerinckia, Beneckea, Brachymonas, Bradyrhizobium, Burkholderia, Caryophanon, Caulobacter, Chloroflexus, Chlorogloea, Chromatium, Chromobacterium, Clostridium, Comamonas, Corynebacterium, Cupriavidus, Cyanobacterium, Defluviicoccus, Derxia, Delftia, Ectothiorhodospira, Erwinia, Escherichia* (recombinant and wild type), *Ferrobacillus, Gamphospheria, Gloeocapsa, Gloeothece, Haemophilus, Halobacterium, Haloarcula, Haloferax, Halomonas, Haloquadratum, Haloterrigena, Hydrogenophaga, Hyphomicrobium, Klebsiella* (recombinant), *Lamprocystis, Lampropedia, Leptothrix, Legionella, Methanomonas, Methylobacterium, Methylosinus, Methylocystis, Methylomonas, Methylovibrio, Micrococcus, Microcoleus, Microcystis, Microlunatus, Microvoleus, Moraxella, Mycoplana, Nitrobacter, Nitrococcus, Nocardia, Nostoc, Oceanospirillum, Oscillatoria, Paracoccus, Paucispirillum, Pedomicrobium, Photobacterium, Protomonas, Pseudomonas, Ralstonia, Rhizobium, Rhodobacter, Rhodococcus, Rhodopseudomonas, Rhodospirillum, Rubrivivax, Saccharophagus, Shinorhizobium, Sphaerotilus, Spirillum, Spirulina, Staphylococcus, Stella, Thiocystis, Thiodictyon, Thiopedia, Thiosphaera, Variovorax, Vibrio, Wautersia* (today *Cupriavidus*), *Xanthobacter*, and *Zoogloea*.

The nature of the PHAs produced depends on the microbial strain used and the carbon sources in the wastewater concentrate which serve as nutrients supporting bacteria growth and accumulation. Suitable nutrients include sugars, such as fructose, glucose, xylose, sucrose, lactose; organic acids, such as Volatile Fatty Acids (VFAs), including acetic acid, propionic acid, and butyric acid, lactic acid, lauric acid, myristic acid, oleic acid, palmitic acid, stearic acid, valeric acid, and 4-hydroxyhexanoic acid; alcohols and polyalcohols, such as glycerol and 1,3-butanediol; and gases, such as methane and carbon dioxide. It has been found that small molecules such as alcohols, VFAs and sugars are effectively isolated from wastewater by the filtration/reverse osmosis process described herein. Thus, a typical wastewater concentrate produced using the methods of the invention will include many of these nutrients and can therefore serve as a source for bacterial PHA production.

In a preferred embodiment, the wastewater is OMW and the RO concentrate comprises sugars and VFAs.

Bacterial species that are able to effectively accumulate PHAs from such carbon sources include *Azohydromonas australica*, *Azohydromonas lata* (former *Alcaligenes latus*), *Azotobacter beijerinckii*, *Azotobacter chrococcum*, *Azotobacter vinelandii*, *Bacillus megaterium*, *Bacillus* sp., *Burkholderia cepacia* (former *Pseudomonas multivorans* and *Pseudomonas cepacia*), *Caulobacter vibrioides*, *Comamonas* sp., *Cupriavidus necator* (former *Hydrogenomonas eutropha*, *Alcaligenes eutrophus*, *Ralstonia eutropha* and *Wautersia eutropha*), *Halomonas boliviensis*, *Hydrogenophaga pseudoflava*, *Novosphingobium nitrogenifigen*, *Pseudomonas aeruginosa*, and *Rhizobium meliloti*.

In a preferred embodiment, the bacterial species used in the method of the invention is *Azotobacter vinelandii*. In another preferred embodiment, the bacterial strain used in the present invention is *Azotobacter vinelandii* UWD. In the absence of other monomers added to the natural carbon source, the polymer accumulated by *Azotobacter vinelandii* species is poly-3-hydroxy-butyrate (PHB) a short-chain-length (scl) PHA. In certain embodiments, specific monomers other than 3-hydroxy-butyrate (3-HB) are added to the bacterial digest. A non-limiting example of such an additional monomer is 3-hydroxyvalerate (3-HV), which leads to the production of the copolymer poly(3-HB-co-3-HV) (PHB-HV). The percentage of HV monomers in the final PHB-HV co-polymer can be chosen to confer on the copolymer product desired properties, such as desired thermomechanical properties. Certain bacterial species, such as *Cupriavidus necator*, directly produce co-polymers from the natural carbon source without the addition of exogenous hydroxy-acid monomer.

In the present invention, the bacterial production of the biopolymer, such as PHA, consists of an anaerobic digestion and an aerobic digestion step, each of which is preferably carried out in a different bioreactor. Each step is preferably subject to suitable temperature and pH controls as are known in the art. The stream subjected to the digestion steps is the RO concentrate described above, optionally combined with other concentrates, for example, the UF concentrate and/or the NF concentrate.

In one embodiment, the initial feed is subjected to anaerobic digestion, which increases the concentration of VFAs by partial sugar fermentation, producing mainly acetic, propionic and butyric acid through a process known as acidogenesis. This procedure allows the bacteria to undergo diauxic growth in the second aerobic digestion. A fresh sludge containing mixed microbial cultures is added as an inoculum to the initial feed to start the anaerobic digestion and the acidogenesis. The sludge is preferably an industrial, urban or farm sludge, for example, a sludge from an urban water treatment plant. The sludge initiates the anaerobic digestion process. In a preferred embodiment of the present invention, anaerobic conditions are produced by bubbling inert gas, such as helium or argon, into the starting mixture.

The temperature and initial pH value are selected to maximize the acidogenesis yield and depend on the composition of the starting feed. In a preferred embodiment, the pH of the OMW RO concentrate, optionally mixed with UF and/or NF concentrate, ranges from 4.5 to 6.0, and the temperature is maintained at the desired value by a thermostatic bath. In certain embodiments, the temperature is maintained in the range of 25-45° C., preferably at about 37° C.

In another preferred embodiment, the acidogenic phase is run for a period of time sufficient to increase the concentration of VFAs in the solution. In certain embodiments, the acidogenic phase is run from about 24 to about 48 hours, preferably from about 24 to about 30 hours, and more preferably for about 27 hours. At the end of this time, the anaerobically digested solution is subjected to aerobic digestion, optionally following further treatment, after inoculation with the selected bacterial strain.

In a preferred embodiment, the anaerobically digested solution is further treated prior to the aerobic digestion to eliminate suspended solids, to adjust the pH and/or to be physically sterilized. For example, in certain embodiments, the anaerobically digested solution is centrifuged at a speed high enough and for a time sufficient to remove coarse solid particles which may be suspended in the solution, preferably at a speed in the range of 2000-9000 rpm for 2 to 20 minutes, and more preferably at 8000 rpm for 10 minutes. In another preferred embodiment, the pH of the supernatant resulting from centrifugation is adjusted to a value in the range of about 6.0 to 8.0, more preferably to about 7.0. In certain embodiments, the pH is adjusted by addition of a basic aqueous solution, such as an aqueous sodium hydroxide or ammonium hydroxide solution or any other base. Ammonium hydroxide can also serve as a nitrogen source in the solution. In another preferred embodiment, the pH-adjusted solution is sterilized by physical membrane filtration to avoid growth of microorganisms other than the selected bacterial strain in the aerobic digestion phase. For example, polymeric membranes with pore dimensions no larger than 0.2 μm can be used for physical sterilization.

In a preferred embodiment, the anaerobically digested solution, optionally following the further treatment as discussed above, is sent to a second bio-reactor to be aerobically digested after the inoculation with the selected bacterial strain.

Applicants have found that the filtration/RO process described herein is able to generate an RO concentrate that is 5 to 7 times more concentrated in sugars and other small molecules than the starting wastewater, thus providing a highly desirable concentrated nutrient medium for production and intracellular accumulation of bacterial biopolymers, such as PHAs.

In a preferred embodiment of the present invention, the anaerobically digested solution, following pH adjustment and sterilization as described above, is diluted with deionized water to obtain the optimal conditions for PHAs production in the aerobic digestion phase. In a preferred embodiment, the ratio of the volume of the anaerobically digested solution to the volume of deionized water added is in the range of 1.0 to 99.0%. In another preferred embodiment, this ratio is below 70% v/v, preferably in the range of 10 to 50% v/v. In another preferred embodiment, the ratio is in the range of 20 to 40% v/v. The lower the dilution of the waste stream concentrate, the lower the volume necessary to produce the same quantity of biopolymer, such as PHA, from an equal starting quantity of wastewater.

According to the present invention, the optionally diluted anaerobically digested waste stream concentrate after pH adjustment and sterilization is subjected to aerobic digestion following inoculation with the selected bacterial strain. In a preferred embodiment, the bacterial strain is *Azotobacter vinelandii* UWD. The selected bacteria strain is pre-grown in the same medium, i.e. the anaerobically digested waste stream concentrate, prior to being added to the bio-reactor to obtain the desired cell density for inoculation. In another preferred embodiment, an inoculum of $10^6$ cell/mL is used. The aerobic digestion is preferably continued for a sufficient time to maximize the accumulation of biopolymer, such as intracellular PHAs and avoiding the lysis of bacteria cells which can occur at too long an incubation time with the consequent dispersion of the accumulated biopolymer into the growth medium. In a preferred embodiment, the incubation is carried out in the range of about 24 to 120 hours. In a more preferred embodiment, the incubation is carried out from about 48 to 96 hours.

At the end of the aerobic incubation, the intracellular accumulated biopolymer, for example, PHA, granules are extracted to recover the biopolymer product. In a preferred embodiment, the biomass resulting from aerobic digestion, which includes bacterial cells and intracellular accumulated biopolymer, is isolated by centrifugation, washed preferably with phosphate buffer solution and dried, for example in vacuum or by lyophilization. The dried biomass is then preferably subjected to an extraction process involving lysis of the bacterial cell membrane to extract the intracellular biopolymer granules. Suitable methods for extracting PHAs include solvent extraction, using, for example, chlorinated solvents such as chloroform, dichloromethane, 1,2-dichloroethane, or acetone and 1,2-propylene carbonate, or non-halogenated solvents, such as methyl-t-butyl ether, isoamyl propionate, isoamyl valerate and propyl butyrate; non-solvent digestion methods, for example, using surfactants or salts such as sodium hypochlorite; mixed solvent-digestion extraction; enzymatic digestion; supercritical fluid (SCF) extraction using, for example, supercritical carbon dioxide, ammonia, or methanol; mechanical extraction, for example, using a beads mill or high pressure homogenization; sonication or gamma radiation exposure.

The selected extraction method affects the chemical properties of the extracted biopolymer properties. In a preferred embodiment of the present invention, the extraction method is selected to maximize the extraction yield while maintaining desired properties of the extracted biopolymer and preferably maintaining an ecologically benign process.

When the biopolymer is PHA, it is isolated in the form of a white powder and can be processed with conventional plastic manufacturing procedures. Applicants have found that the PHA produced by the process above described, i.e. bacterial digestion by *Azotobacter vinelandii* UWD of the RO concentrate of OMW, is poly(3-hydroxybutyrate).

The PHAs produced as described above can be used as matrices in bio-composites where the additives include natural agents which are products of the same process used to produce the PHAs. In a preferred embodiment, such additives are recovered in the MF concentrate. The invention, however, also contemplates recovering natural additives from the wastewater stream using other methods, including centrifugation.

Once the natural additives have been recovered and PHA bio-matrix produced according to aforementioned methods, they are combined to obtain the desired composite. The natural additives can be added to the biopolymer matrix in different amounts and morphologies depending on the intended application of the composite. Moreover, the preparation of the composite can be accomplished by a number of techniques. In a preferred embodiment of the present invention, the composite is prepared in the form of a thin film by casting from a suspension with a concentration of PHA ranging from 0.1 to 20% w/w with respect to the weight of solvent, preferably between 1 and 5% w/w, and an appropriate additive concentration, for example, from 0.1 to 49.9% w/w with respect to the total mass of the PHA and additives, preferably from 10 to 40% w/w, in a solvent or solvent mixture which is able to dissolve PHA, including fluorinated organic solvents, such as 1,1,1,3,3,3-hexafluoro-2-propanol and chlorinated organic solvents, such as chloroform and dichloromethane.

In other preferred embodiments, the composite is prepared without using an organic solvent. For example, the PHA matrix can be heated to its melting temperature, typically in the range of 170-180° C., or to a lower temperature with the concomitant application of a mechanical pressure to induce PHA melting, to homogenize the final composite. In this embodiment, the PHB matrix, when heated and optionally pressed to melt, acts as a viscous dispersing matrix for the natural additives, and can be manipulated, homogenized and cooled to room temperature in the desired form, preferably in the form of a sheet or different shaped containers which can be used for preparation of agricultural items and packaging. Suitable techniques for preparing the composite, with no or limited use of organic solvents, include, but are not limited to, hand/wet lay-up methods, extrusion, pultrusion, welding, compounding, lamination, compression, injection and vacuum bag molding, and hot press.

In a preferred embodiment, the natural additives are added in the form of a finely micro-sized substantially monodisperse powder. In another preferred embodiment, sizing of the natural additives recovered by MF is achieved by subjecting the dried aggregated powder to mechanical pressure and, optionally, to high energy beads milling. Other forms of the additives are suitable for preparing composites depending on the pretreatment of the natural additives after being isolated from the wastewater and prior to being added to the PHA matrix in the final composite.

Because the PHA matrix and the natural additives have opposite solubility properties, coupling agents and plasticizers can optionally be used to improve the interfacial adhesion between them. In certain embodiments, such agents are selected to preserve the green nature, biodegradability, compostability and/or biocompatibility of the final bio-composite. Examples of such agents include but are not limited to glycerol. In a preferred embodiment, glycerol is used as a natural coupling agent and plasticizer to increase the solubility of the additives into the PHA matrix and to improve the mechanical properties of the final composite in terms of plasticity by decreasing the brittleness of PHA. Glycerol is an abundant natural chemical present in glycerides (mono-, di- and tri-), the natural form of fatty acids, and moreover is a byproduct of biodiesel production (10% w/w with respect to final biodiesel), thus being an ideal candidate to be used as an agent in a green bio-composite.

The use of glycerol in the final bio-composite, preferably in a percentage of 0.1 to 30% w/w with respect to PHA and more preferably in the range of 7-25%, greatly reduces the brittleness of the final product, making it amenable to being shaped in various forms by conventional plastic fabrication techniques. The use of glycerol or other agents to improve the bio-composite properties is optional.

The MF natural additives composition, with lignin and cellulose fractions being the major components, is suitable to confer different properties to the biopolymer matrix, in terms of modulation of stiffness or softness of the final composite. Such a product has different properties than the biopolymer matrix itself. The mass and the morphology of natural additives incorporated into the final biopolymer matrix composite may be varied in order to obtain the target mechanical properties for the desired application of the composite while maintaining its complete bio-degradability and compostability. The latter properties are indeed of great importance for the final composite and its application in agriculture and packaging. PHA matrix itself is able to be completely degraded within six months not only in landfills but also in lakes, marine water and soil. PHA matrix degradation allows the dispersion of natural additives contained in the composite in the environment. Applicants have found that this behavior increases the compostability of the composite object of the present invention, since the natural additives recovered by MF or other aforementioned techniques from the starting wastewater are suitable materials to be used as compost. Thus the benefit of using this bio-composite in the applications better described below is related with the high capability of the bio-composite waste material at the end of the product life cycle to be disposed and bio-degraded completing the bio-transformation cycle with a quasi-zero $CO_2$ emission, i.e. quasi-neutral carbon cycle. Applicants have found that the present invention provides an advantageous all-natural material that is also industrially relevant in terms of costs. In fact, the bio-composite object of the present invention is suitable to be used as alternative material to the PHA-based products. One of the main limit of PHA market adoption is surely related to its high price, which limits its usage as alternative to fossil carbon-derived polymers such as polyethylene, polypropylene, polystyrene, polyethyleneterephthalate etc. The market potential cost of the natural additives extracted from the wastewater stream in the present invention is roughly three orders of magnitude lower than the market price of PHA per mass unit, when these natural additives are sold as compost materials. Since these natural additives are used in the final composite in percentages up to 50% in mass the composite cost can be reduced down to one half with respect to PHA itself per mass unit. Thus, a product made of the composite object of the present invention is less expensive than the corresponding product made of pure PHA, while preserving the biodegradability properties, with an improved compostability, and with the possibility of tuning mechanical properties.

In one embodiment, the invention relates to a biopolymer composite. In one embodiment, the biopolymer composite is produced by produced by a method of the invention.

In certain embodiments the biopolymer composite comprises PHA, such as poly(3-hydroxybutyrate) or poly(3-hydroxybutyrate-co-3-hydroxyvalerate). In certain embodiments, he biopolymer composition preferably further comprises organic microparticles comprising, for example, lignin and/or cellulose. In certain embodiments, the microparticles are of a dimension in the range of 0.1 to 100 µm. In one embodiment, the microparticles are present in the composite in an amount of 0.1 to 49.9% w/w with respect to the total mass of the PHA and microparticles, preferably from about 10 to about 40% w/w.

The bio-composite of the present invention can be used in the preparation of a range of products with application, for example, in agriculture and generally in packaging. In particular, conventional plastic items with a short life-cycle which are destined to be disposed of in landfills and generate a large volume of waste or that come in contact with soil and must be removed to prevent environmental pollution can be advantageously made with the subject bio-composite. The main advantage is that at the end of the product life the bio-composite is degraded by natural anaerobic and aerobic microbial degradation processes and can therefore be safely disposed in the environment without generating polluting residues. Thus the material is efficiently biodegraded; this is advantageous for agricultural items which are in contact with soil and plants as they do not need to be removed after their use but can be simply left in their usage site until completely bio-degraded. With respect to pure PHA based materials they are less expensive and can deliver organic material to the soil, that is, the natural additives contained in the composite released upon biodegradation of the biopolymer matrix.

Examples of products which can be made with the composites of the invention include, but are not limited to, storage and packaging containers, films, bags, cups, plates, cutlery, and agricultural items. Example of agricultural items which can be made with the composites of the invention include, but are not limited to, transplanter containers and sub-ground pots that can be left in soil after leaving the plant in the soil being biodegraded over time; covering films for erosion and moisture control and mulches that do not need to be removed after the plant growing period; bags, nets and twines that come in contact with soil and plants or seeds; films, wraps or bags for seeds, with a controlled degradation time, which can be used to protect the seed from harsh conditions or from birds; various agricultural items which are pre-loaded with chemical or bio-active substances for controlled slow release of such substances into the soil upon biodegradation of the biopolymer composite; and films as covers or tents for greenhouses or for hydroponic cultivation to regulate moisture, temperature and UV exposure of plants.

The foregoing products are conveniently produced using the bio-composite of the invention as raw material in place of pure PHA, with the possibility of tuning mechanical properties by adjusting the amount of natural additives in the bio-composite, with improved biodegradability and compostability of the waste material at the end of product life cycle and with a lower cost of the raw material.

The benefits of using the bio-composite of the invention in the aforementioned applications are combined with the advantage of producing such a plastic, bio-degradable, compostable and low-cost raw material from a unique wastewater stream by the integrated process described herein. Thus an industrially applicable material in terms of cost and performance such as the bio-composite of the invention is environmentally safe and is produced with a carbon-neutral process and does not generate pollution. In fact, the production of the biocomposite effectively reduces pollution by efficiently treating and extracting value from wastewater streams from industrial processes.

EXEMPLIFICATION

Olive mill wastewater (OMW) was passed at a rate of 10 L/h through large pore filters (0.5 mm pore size) to remove coarse suspended solids and limit membrane fouling in subsequent steps. The pretreated OMW was then subjected to microfiltration (MF), ultrafiltration (UF) and reverse osmosis (RO), by means of diafiltration techniques. All processes were carried out at controlled temperature (20° C., using a heat exchanger) and under an $N_2$ atmosphere. A tubular polypropylene membrane (cut-off 0.1-0.3 µm) with a total area of 8 $m^2$ was used for microfiltration. Two spiral membranes made of polyamide and traces of polysulfone with a cut-off of 7 kDa and a total area of 16 $m^2$ were used for ultrafiltration. A spiral thin-film membrane (TFM) composed of Durasan™ and polysulfone with a total area of 9 m² was used for reverse osmosis. Characteristics of the original olive mill waste stream, the microfiltration permeate (MFP) and the reverse osmosis concentrate (ROC) are set forth in the table below.

|  | COD (mg/L) | Total N (g/L) | pH | Reducing Sugars (g/L) |
| --- | --- | --- | --- | --- |
| OMW | 81568 | 0.93 | 5 | 0.74 |
| MFP | 77344 | 0.3 | 4.96 | 1.09 |
| ROC | 331360 | 0.98 | 5.26 | 8.4 |

The MF concentrate was recovered in the form of a dense brown-greenish sludge, then dried in air and eventually finely homogenized in high energy beads mill. Solid state FT-IR (3400 cm-1 broad band vO-H; 2925, 2855 cm$^{-1}$ vC-H; 1745, 1630 cm$^{-1}$ vC=O; 1550-800 cm$^{-1}$ vC=N+ vC=C+vC-N+vC-O+vC-C; vC-H+vO-H+vN-H; strong absorption band centered at 1050 cm$^{-1}$ typical of carbohydrates, polysaccharides, and aromatic ethers) and TGA (dynamics: 5° C.-900° C. at 10° C./min; $N_2$ flow: 50 mL/min) analyses on the isolated solid showed the presence of cellulose, hemicellulose and lignin.

The RO concentrate was treated by solid phase extraction in order to remove soluble polyphenols, lowering their final concentration to 0.15 g/L. Total reducing sugar concentration in the RO concentrate was measured to be 8.4 g/L, with a pH of 5.26. The anaerobic digestion was carried out in a glass bio-reactor equipped with a thermostat and a gas inlet and outlet. The RO concentrate was poured into the bio-reactor and activated fresh sludge was added (10% w/w with respect to initial COD value) to start the anaerobic fermentation. Prior to starting the fermentation the medium was purged for 20 minutes with helium to eliminate dissolved oxygen. The anaerobic digestion was run at 37° C. for a selected time, typically between 24 and 48 hours, under continuous gently stirring. At the end of this time the digested stream was centrifuged at 8000 rpm for 10 minutes and sterilized by passing the stream through a polymeric membrane with a pore size of 0.2 μm. The resulting medium was diluted to the desired concentration (e.g. 20%, 40%, 60%, 80% v/v) with twice-distilled water and the pH was adjusted to 7.2 by adding dropwise a concentrated solution of $NH_4OH$ under sterile conditions.

The diluted medium was used as substrate for the aerobic digestion by *Azotobacter vinelandii* UWD strain which was inoculated at a concentration of $10^6$ cell/mL, after being pre-grown in the same liquid stream. The aerobic digestion was continued for the desired time to maximize the accumulation of intracellular PHAs and was typically in the range of 24 to 120 hours. At the end of this period the solid biomass was recovered by centrifugation at 8000 rpm for 10 minutes and lyophilized. The solid poly(hydroxybutyrate) (PHB) accumulated in the cells was extracted by a modification of conventional extraction methods, using an aqueous NaClO solution to weaken the cell membrane and facilitate membrane breakage for the recovery of intracellular biopolymer. The resulting PHB was optionally purified by crystallization. The isolated solid was analyzed by $^1$H-NMR (600 MHz, $CDCl_3$: 5.24 sex, 1H; 2.51, m, 2H; 1.25, d, 3H), confirming the structure of the obtained polymer to be poly-3-hydroxybutyrate. Thermal analyses (m.p.=175° C. (DSC), Tg=3-4° C. (DSC), Td=274° C. (TGA)) further confirmed the nature of the product obtained.

The solid material isolated from the MF step as described above was used as an additive in the desired percentage for the PHB-matrix composite. In a typical procedure PHB (200 mg), produced from the aforementioned microbial digestion of OMW, and glycerol (20 mg) were dissolved in 1,1,1,3,3,3-hexafluoro-2-propanol with sonication and gentle heating to a final PHB concentration of 2% w/w. After the complete dissolution of PHB, the solid material isolated from MF (80 mg) was added to the solution and the solution was vigorously stirred until a homogeneous viscous dispersion was obtained. The PHB-based polymer composite was shaped in the form of thin films (5-20 μm thick) by casting the dispersion into petri dishes and heating at 60° C. for several minutes until the complete evaporation of the solvent.

While this invention has been particularly shown and described with references to preferred embodiments thereof, it will be understood by those skilled in the art that various changes in form and details may be made therein without departing from the scope of the invention encompassed by the appended claims.

We claim:
1. A method of producing a biopolymer, comprising the steps of:
   (a) subjecting wastewater comprising organic carbon and organic solids to:
      (i) microfiltration, thereby producing a first permeate and a concentrate; and optionally further subjecting the first permeate to at least one process selected from
      (ii) ultrafiltration; and
      (iii) nanofiltration;
      wherein each of steps (ii) and (iii) produces a further permeate comprising organic carbon and a further concentrate, wherein the permeate of the final of steps (i), (ii) and (iii) is the final permeate; and the input for each of steps (ii) and (iii) is the permeate of the immediately preceding step;
   (b) subjecting the final permeate to reverse osmosis, thereby producing a final concentrate, wherein said final concentrate comprises organic carbon;
   (c) subjecting the final concentrate to a biological process comprising microbial aerobic digestion that produces a biopolymer, thereby producing a biomass comprising the biopolymer; and
   (d) isolating the biopolymer from the biomass.
2. The method of claim 1, wherein in step (c) the biological process further comprises anaerobic digestion.
3. The method of claim 1, wherein the wastewater is olive mill wastewater.
4. The method of claim 1, wherein the biopolymer is a poly(hydroxyalkanoate).
5. The method of claim 1, wherein prior to step (a), the wastewater is treated to remove one or both of coarse suspended solids and emulsions.
6. A method of producing a biopolymer matrix composite, comprising the steps of:
   (a) providing wastewater comprising organic carbon and organic solids;
   (b) subjecting the wastewater to
      (i) microfiltration, thereby producing a first permeate and a concentrate; and optionally further subjecting the first permeate to at least one process selected from:
      (ii) ultrafiltration; and
      (ii) nanofiltration;

wherein each of steps (ii) and (iii) produces a further permeate comprising organic carbon and a further concentrate, wherein the permeate of the final step is the final permeate; and the input for steps (ii) and (iii) is the permeate of the immediately preceding step;

(c) subjecting the final permeate to reverse osmosis, thereby producing a final concentrate, wherein said final concentrate comprises organic carbon;

(d) isolating microparticles from the concentrate of step b(i);

(e) subjecting the final concentrate to a biological process comprising aerobic digestion, thereby producing a biopolymer; and (f) combining the biopolymer and the microparticles of step (d), thereby producing the biopolymer matrix composite.

7. The method of claim 6, wherein the biopolymer and the microparticles are combined in the presence of at least one additive selected from coupling agents and plasticizers.

8. A method of producing a biopolymer matrix composite, comprising the steps of:

(a) subjecting wastewater comprising organic carbon and organic solids to:
  (i) microfiltration, thereby producing a permeate and a concentrate; and optionally further subjecting the permeate to at least one process selected from:
  (ii) ultrafiltration; and
  (iii) nanofiltration;
wherein each of steps (ii) and (iii) produces a further permeate comprising organic carbon and a further concentrate; and the input for each of steps (ii) and (iii) is the permeate of the immediately preceding step; and wherein the permeate of the final of steps (i), (ii) and (iii) is the final permeate;

(b) subjecting the final permeate to reverse osmosis, thereby producing a final concentrate, wherein said final concentrate comprises organic carbon;

(c) isolating microparticles from the concentrate of step a(i);

(d) subjecting the final concentrate to anaerobic digestion;

(e) subjecting the product of step (d) to aerobic digestion by a microorganism to produce a biomass comprising a biopolymer;

(f) isolating the biopolymer from the biomass; and (g) combining the biopolymer and the microparticles of step (d), thereby producing the biopolymer matrix composite.

9. The method of claim 8, wherein the microorganism of step (e) comprises one or more species selected from *Acidovorax, Acinetobacter, Actinobacillus, Actinomycetes, Aeromonas, Alcaligenes, Allochromatium, Anabaena, Aphanothece, Aquaspirillum, Asticcaulus,Axobacter, Azomonas, Aureobasidium, Azohydromonas, Azospirillum, Azotobacter, Bacillus, Beggiatoa, Beijerinckia, Beneckea, Brachymonas, Bradyrhizobium, Burkholderia, Caryophanon, Caulobacter, Chloroflexus, Chlorogloea, Chromatium, Chromobacterium, Clostridium, Comamonas, Corynebacterium, Cupriavidus, Cyanobacterium, Defluviicoccus, Derxia, Delftia, Ectothiorhodospira, Erwinia,* recombinant and wild type *Escherichia, Ferrobacillus, Gamphospheria, Gloeocapsa, Gloeothece, Haemophilus, Halobacterium, Haloarcula, Haloferax, Halomonas, Haloquadratum, Haloterrigena, Hydrogenophaga, Hyphomicrobium,* recombinant *Klebsiella, Lamprocystis, Lampropedia, Leptothrix, Legionella, Methanomonas, Methylobacterium, Methylosinus, Methylocystis, Methylomonas, Methylovibrio, Micrococcus, Microcoleus, Microcystis, Microlunatus, Microvoleus, Moraxella, Mycoplana, Nitrobacter, Nitrococcus, Nocardia, Nostoc, Oceanospirillum, Oscillatoria, Paracoccus, Paucispirillum, Pedomicrobium, Photobacterium, Protomonas, Pseudomonas, Ralstonia, Rhizobium, Rhodobacter, Rhodococcus, Rhodopseudomonas, Rhodospirillum, Rubrivivax, Saccharophagus, Shinorhizobium, Sphaerotilus, Spirillum, Spirulina, Staphylococcus, Stella, Streptomyces, Synechococcus, Syntrophomonas, Thiobacillus, Thiocapse, Thiococcus, Thiocystis, Thiodictyon, Thiopedia, Thiosphaera, Variovorax, Vibrio, Cupriavidus, Xanthobacter,* and *Zoogloea*.

10. The method of claim 8, wherein step (a) consists of microfiltration and ultrafiltration.

11. The method of claim 10, wherein the final concentrate is combined with the ultrafiltration concentrate prior to conducting step (e).

12. The method of claim 8, wherein step (a) consists of microfiltration, ultrafiltration and nanofiltration.

13. The method of claim 12, wherein the final concentrate is combined with the ultrafiltration concentrate and the nanofiltration concentrate prior to conducting step (e).

14. The method of claim 8, further comprising the step of drying the microparticles of step (c).

15. The method of claim 14, further comprising the step of homogenizing the dried microparticles.

16. The method of claim 8, wherein step (g) comprises the steps of:
  (i) dissolving the biopolymer in a solvent thereby forming a biopolymer solution;
  (ii) suspending the microparticles in the biopolymer solution, thereby forming a suspension; and
  (iii) removing the solvent, thereby forming the composite.

17. The method of claim 16, wherein the biopolymer is a PHA and the solvent is an organic solvent.

18. The method of claim 8, wherein step (g) comprises:
  (i) melting the biopolymer;
  (ii) dispersing the microparticles in the melted biopolymer to form a dispersion; and
  (iii) cooling the dispersion, thereby forming the composite.

19. The method of claim 8, further comprising the step of isolating the biomass from the product of aerobic digestion.

20. The method of claim 8, wherein the biomass comprises bacterial cells having intracellular biopolymer and step (f) comprises extracting the biopolymer from the cells.

* * * * *